(12) United States Patent　(10) Patent No.: US 8,369,917 B2
Wang　(45) Date of Patent: Feb. 5, 2013

(54) FINGER-CLIPPED OXIMETER WITH FINGER PRESSED PLATE

(75) Inventor: Weihu Wang, Beijing (CN)

(73) Assignee: Beijing Choice Electronic Technology Co., Ltd., Beijing (CN)

( * ) Notice: Subject to any disclaimer, the term of this patent is extended or adjusted under 35 U.S.C. 154(b) by 259 days.

(21) Appl. No.: 12/865,084

(22) PCT Filed: May 20, 2008

(86) PCT No.: PCT/CN2008/071022
§ 371 (c)(1),
(2), (4) Date: Jul. 28, 2010

(87) PCT Pub. No.: WO2009/140815
PCT Pub. Date: Nov. 26, 2009

(65) Prior Publication Data
US 2010/0331635 A1　Dec. 30, 2010

(51) Int. Cl.
*A61B 5/00* (2006.01)
(52) U.S. Cl. ...................................... 600/344
(58) Field of Classification Search .................. 600/323, 600/340, 344
See application file for complete search history.

(56) References Cited

U.S. PATENT DOCUMENTS

| 4,913,150 | A | 4/1990 | Cheung et al. | |
|---|---|---|---|---|
| 5,490,523 | A | 2/1996 | Isaacson et al. | |
| 5,810,724 | A | 9/1998 | Gronvall | |
| 6,154,667 | A * | 11/2000 | Miura et al. | 600/323 |
| 7,254,434 | B2 * | 8/2007 | Schulz et al. | 600/344 |
| 7,548,771 | B2 * | 6/2009 | Mannheimer | 600/323 |
| 7,657,294 | B2 * | 2/2010 | Eghbal et al. | 600/344 |
| 2003/0045784 | A1 | 3/2003 | Palatnik et al. | |
| 2010/0036218 | A1 | 2/2010 | Wang et al. | |

FOREIGN PATENT DOCUMENTS

| CN | 2785542 Y | 6/2006 |
|---|---|---|
| CN | 1961827 A | 5/2007 |
| CN | 101015455 A | 8/2007 |
| JP | 2000262496 A | 9/2000 |

* cited by examiner

*Primary Examiner* — Rodney Fuller
(74) *Attorney, Agent, or Firm* — The Webb Law Firm

(57) ABSTRACT

A finger-clipped oximeter includes an upper case (2) in which a measuring element (4), a data processing circuit, batteries (6) and a display (3) are provided, a rectangular through hole being provided in the upper case (2); a finger pressed plate (10) in which a measuring element is also provided, a finger inserting hole (11), a rectangular column (7) with a position corresponding to that of the rectangular through hole of the upper case (2); and a pair of connectors which are capable of ascending or descending, each of the connectors including one U-shaped connecting rod (8).

9 Claims, 5 Drawing Sheets

FINGER-CLIPPED OXIMETER WITH FINGER PRESSED PLATE

FIELD OF THE INVENTION

The present invention relates to a finger-clipped oximeter, and particularly relates to a finger-clipped oximeter with a finger pressed plate.

BACKGROUND OF THE INVENTION

Normally, a finger-clipped oximeter according to the prior art includes an upper case, a lower case and a pivot which connects the upper case and the lower case together, and the upper and lower cases apply a clamping pressure to a nail portion of a measured finger through a coil spring. Therefore, the upper case and the lower case can be rotated relatively around the pivot and be separated from each other by a distance.

However, the coil spring which controls the upper and lower cases is not assembled easily, and is apt to undergo fatigue fracture so that a useful life of the finger-clipped oximeter is reduced.

Additionally, the upper case is connected to the lower case through the structures of the pivot and the coil spring. This kind of connection is neither firm nor reliable. If such finger-clipped oximeter falls off inadvertently, the upper and lower cases may be separated or disengaged from each other.

Furthermore, the upper case is connected to the lower case through the structures of the pivot and the coil spring so that the upper and lower cases move in the directions which are not parallel to each other, thereby, offering a poor comfort to a user in measurement.

SUMMARY OF THE INVENTION

An object of the present invention is to provide a finger-clipped oximeter, which eliminates the influence of thickness of a finger on the measurement result in such a manner that the lower case is simplified as a structure of an elastic finger pressed plate, so that this kind of finger-clipped oximeter can be suitable for more consumers.

Another object of the present invention is to provide a finger-clipped oximeter, the lower case of which is made of a material of silica gel, so that the measured person feels very comfortable with his finger when the finger-clipped oximeter is being used.

Still another object of the present invention is to provide a finger-clipped oximeter, a finger pressed plate of which applies a measurement force to the finger by peculiar V-shaped springs or magnets, and the useful life of the finger-clipped oximeter can be improved.

Yet still another object of the present invention is to provide a finger-clipped oximeter with a simple structure which can be assembled easily and can operate stably.

For this reason, the present invention provides a finger-clipped oximeter, characterized in that the finger-clipped oximeter comprises: an upper case in which a measuring element, a data processing circuit, batteries and a display are provided, a rectangular through hole being provided in the upper case; a finger pressed plate in which a measuring element is also provided, a finger inserting hole being formed between an upper surface of the finger pressed plate and a lower surface of the upper case; a rectangular column with a position corresponding to that of the rectangular through hole of the upper case being provided on the finger pressed plate; and a pair of connectors which are capable of ascending or descending, each of the connectors including one U-shaped connecting rod, the middle portion of the U-shaped connecting rod being a straight portion which extends through an edge portion on a side of the finger pressed plate, two arm portions of the U-shaped connecting rod being inserted into the upper case to serve as a connecting piece between the upper case and the finger pressed plate.

Preferably, the middle portion of the U-shaped connecting rod is pressure-cast to the edge portion on a side of the finger pressed plate.

Preferably, at least a portion of the middle portion of the U-shaped connecting rod has a structure which can prevent the U-shaped connecting rod from being rotated with respect to the finger pressed plate.

Preferably, at least a portion of the middle portion of the U-shaped connecting rod is made into a pyramid shape or is provided with fins.

Preferably, at least one column like portion which extends straight up is provided at each of four corners of an upper surface of a bottom wall of the upper case, and the positions of the two arm portions of the U-shaped connecting rod are limited by the column like portions.

Preferably, the upper case has a top cover.

Preferably, the finger pressed plate is made of a material of plastics or silica gel.

Preferably, a V-shaped portion which extends toward the middle portion of the U-shaped connecting rod is provided at each end of the two arm portions of the U-shaped connecting rod.

Preferably, the V-shaped portion is opened toward two sides of the U-shaped connecting rod, or is opened toward the straight portion in the middle portion of the U-shaped connecting rod.

Preferably, one movable magnet is provided at each end of the two arm portions of the U-shaped connecting rod, while one stationary magnet is provided at each root of the two arm portions of the U-shaped connecting rod, and the movable magnet and the stationary magnet are provided so that magnetic poles with the same polarity are opposed to each other.

According to the present invention, the lower case is simplified as the structure of the finger pressed plate, a connecting piece between the upper case and the finger pressed plate has an enough stroke under the action of V-shaped springs or the magnetic pole pairs which repel mutually, thereby eliminating the influence of thickness of a finger on the measurement result so that this kind of finger-clipped oximeter can be suitable for more consumers.

According to the present invention, the lower case is made of a material of plastics or silica gel so that the measured person feels very comfortable with his finger when the finger-clipped oximeter is being used.

According to the present invention, the finger pressed plate applies a measurement force to the finger by virtue of a restoring force of the peculiar V-shaped springs or a non-contacting repelling force between the magnets, and the structure of the coil spring in the prior art is cancelled. As a result, the useful life can be improved.

According to the present invention, the structure of the coil spring in the prior art is cancelled, therefore the structure of the finger-clipped oximeter is simple, the finger-clipped oximeter can be assembled easily and can operate stably.

According to the present invention, a certain gap is provided between the rectangular through hole in the upper case and the rectangular column on the finger pressed plate of the finger-clipped oximeter, thus not only the operation is caused to be easy and flexible, but also a certain angle is opened between the finger pressed plate and the upper case to accommodate to the shape of the finger when they rise up or drop down along the rectangular column and the rectangular through hole so that the finger-clipped oximeter can be used more conveniently and comfortably.

According to the present invention, when the finger-clipped oximeter is used in the measurement, the finger pressed plate can apply an appropriate clamping force to the finger by virtue of the restoring force of the V-shaped springs or the non-contacting repelling force between the magnets to ensure effectiveness and accuracy of the measurement.

According to the present invention, the finger pressed plate and the upper case are directed by the rectangular column and the rectangular through hole, and the finger pressed plate and the upper case can always be kept in such a posture as to contact with the finger. When the finger is inserted between the finger pressed plate and the upper case to be measured, a deadlock phenomenon of the conventional oximeter caused by nonparallel movements in the horizontal direction can be eliminated, and the comfort of a user in measurement is improved.

DETAILED DESCRIPTION OF THE PREFERRED EMBODIMENTS

Figure 1:
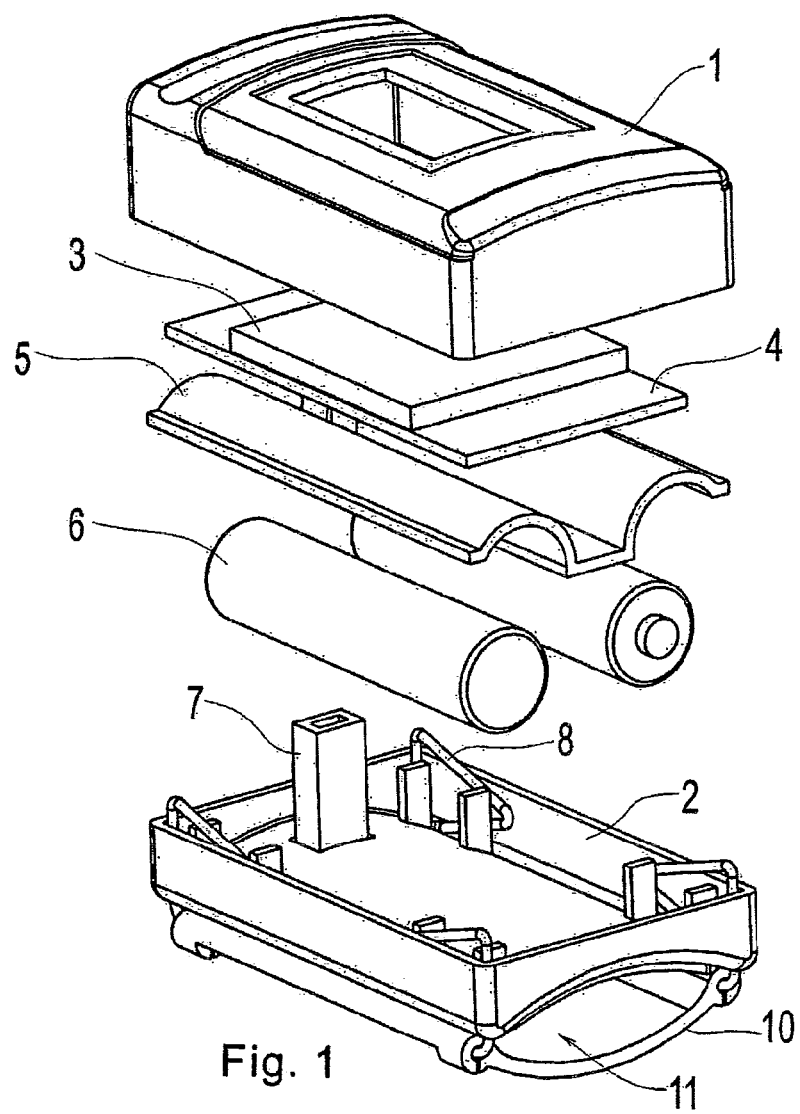
FIG. 1 is an exploded perspective view of a finger-clipped oximeter according to a first embodiment of the present invention.

According to a first embodiment of the present invention, as shown in FIGS. 1 to 5, a finger-clipped oximeter includes a top cover 1, an upper case 2, a display 3, a measuring element 4, a battery jar 5, batteries 6, a rectangular column 7, V-shaped springs 8, a position limited column 9, a finger pressed plate 10 and a finger inserting hole 11, wherein, the rectangular column 7 is fixed on the finger pressed plate 10 and can pass through a rectangular through hole in the upper case 2 to extend into the upper case 2, and a rectangular hole corresponding to the display 3 is provided in the top cover 1.

Figure 2:
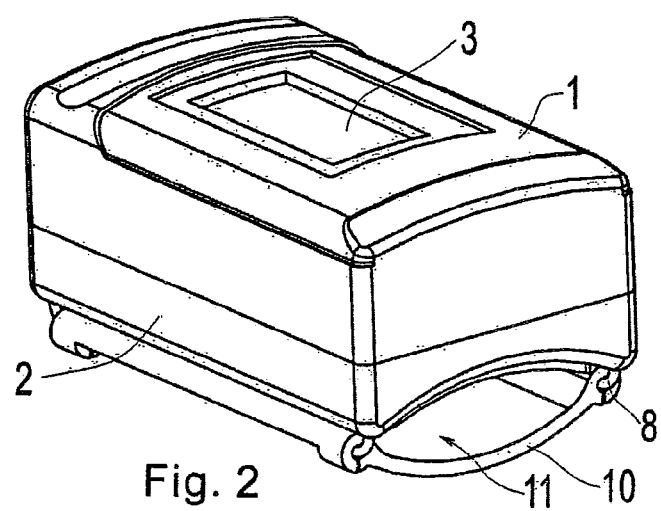
FIG. 2 is an overall perspective view of the finger-clipped oximeter according to the first embodiment of the present invention.
Figure 3:
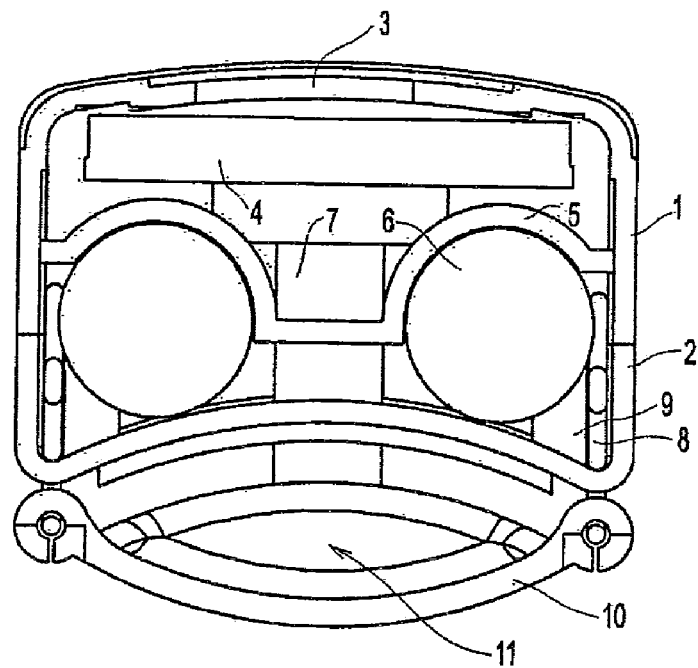
FIG. 3 is a transversal sectional view of the finger-clipped oximeter according to the first embodiment of the present invention.

In this embodiment, as shown in FIGS. 1 to 3, the finger pressed plate 10 can keep contact with a finger following the outline of the finger belly, and the upper case 2 provides a power supply and performs data processing and data display.

Figure 5:
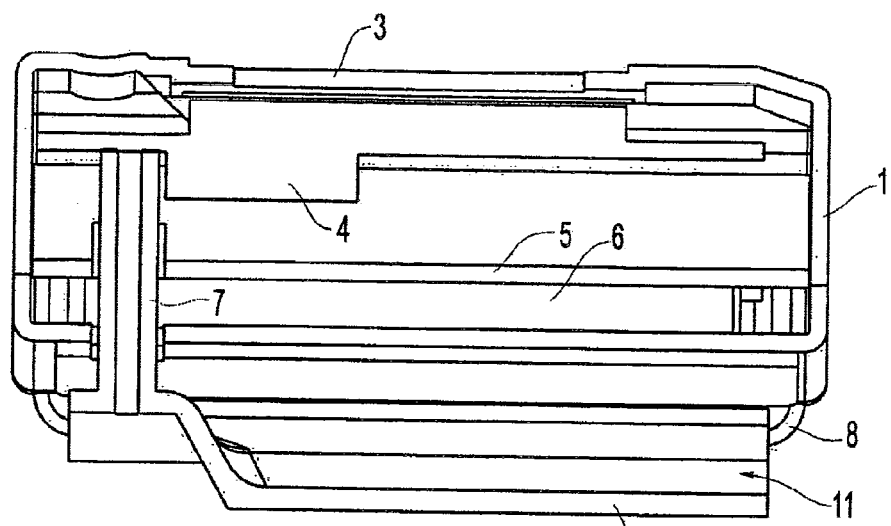
FIG. 5 is another longitudinal sectional view of the finger-clipped oximeter according to the first embodiment of the present invention.

It can be seen most clearly from FIGS. 1 and 5 that the rectangular column 7 is provided on the finger pressed plate 10, the rectangular through hole corresponding to the rectangular column 7 is provided in the upper case 2, and the rectangular column 7 can pass through the rectangular through hole to extend into the upper case 2. The finger pressed plate 10 is directed by the rectangular through hole to ascend or descend, and the state in which the finger pressed plate 10 and the upper case 2 keep close contact with the finger imposes a restriction effect on an ascending or descending stroke of the rectangular column 7. In addition, the rectangular through hole can prevent the finger pressed plate 10 from being rotated excessively around the rectangular column 7; meanwhile, conducting wires of the power supply and signals can pass through the rectangular through hole to be connected to a measuring element (not shown) in the finger pressed plate 10.

Figure 4:
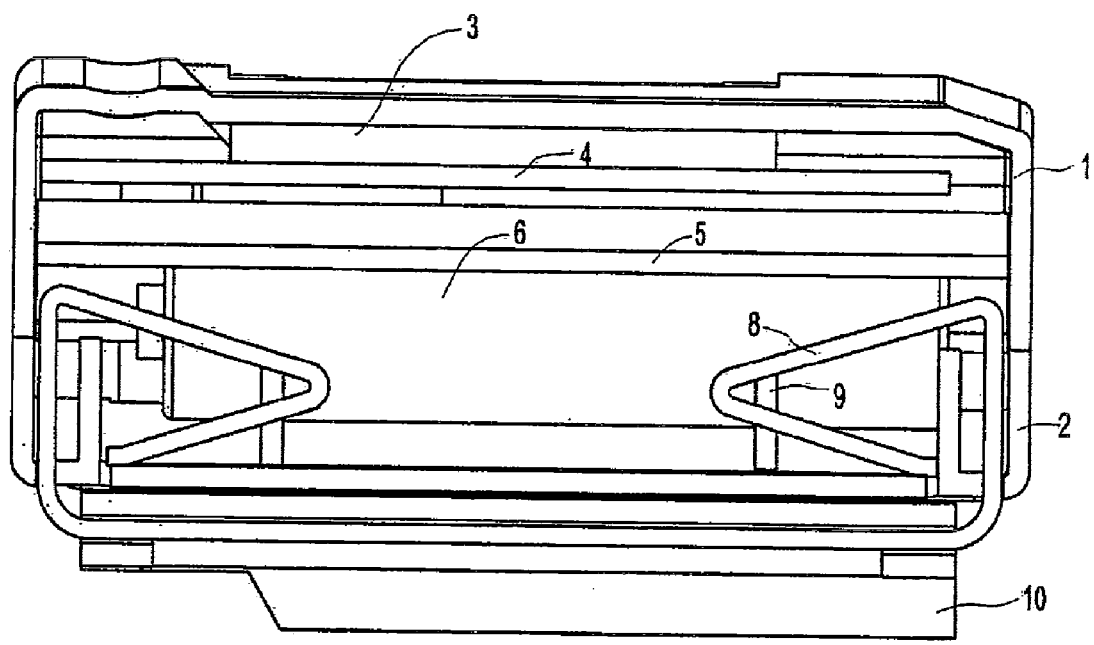
FIG. 4 is a longitudinal sectional view of the finger-clipped oximeter according to the first embodiment of the present invention.

In this embodiment, as shown in FIGS. 1, 3 and 4, one U-shaped connecting rod 8 is provided at each of two longitudinal edges of the oximeter having the finger pressed plate 10 respectively, and the middle portion of each U-shaped connecting rod 8 is a straight portion which extends through an edge to portion on a side of the finger pressed plate 10 and is encased in the finger pressed plate 10. Two arm portions of each U-shaped connecting rod 8 are inserted into the upper case 2 to serve as a connecting piece between the upper case 2 and the finger pressed plate 10, and positions of the two arm portions are limited by the column like portion 9. One V-shaped spring is provided at each end of the two arm portions of each U-shaped connecting rod 8 respectively, therefore in this embodiment, the oximeter having the finger pressed plate 10 is provided with four V-shaped springs totally, that is, one V-shaped spring is provided at each of four corners of a bottom wall of the upper case 2 respectively. The V-shaped springs have a large compression stroke, as a result, both a user with thick fingers and a user with thin fingers can use the oximeter. Further, when the finger pressed plate 10 ascends or descends in a direction which is not parallel to that of the upper case 2 in order to accommodate to the change of thickness from the finger root to the finger tip, the finger pressed plate 10 can be rotated freely around the rectangular column 7 in both the vertical direction and the horizontal direction for a small angle so that the finger is very comfortable during the measurement. Moreover, during this procedure, the V-shaped springs are not influenced by the rotational force but is expanded or contracted in the upper case 2 smoothly so that the finger pressed plate 10 can slide up and down with respect to the upper case 2 smoothly.

According to the first embodiment of the present invention, as shown in FIGS. 1 to 5, the main operation procedure of the finger-clipped oximeter is as follows. When a user inserts a finger into the finger inserting hole 11, the finger pressed plate 10 is pressed downward by the finger belly, and the rectangular column 7 fixed on the finger pressed plate 10 is directed by the rectangular through hole in the upper case 2 to move downward; meanwhile, the V-shaped springs 8 are compressed so as to provide an enough stroke for the finger to be inserted into the finger inserting hole 11.

When the user pulls his finger out of the finger inserting hole 11, the finger pressed plate 10 is not pressed downward by the finger belly any more, and the rectangular column 7 fixed on the finger pressed plate 10 is directed by the rectangular through hole in the upper case 2 to move upward;

meanwhile, the V-shaped springs are restored to their original shapes, and the finger inserting hole 11 is closed.

According to a second embodiment of the present invention, as shown in FIGS. 6 to 10, a finger-clipped oximeter includes a top cover 21, an upper case 22, a display 23, a measuring element 24, a battery jar 25, batteries 26, a rectangular column 27, U-shaped connecting pieces 28, movable magnets 29, stationary magnets 30, a finger pressed plate 31 and a finger inserting hole 32, wherein, the rectangular column 27 is fixed on the finger pressed plate 31 and can pass through a rectangular through hole (as shown clearly in FIG. 6, but not marked) in the upper case 22 to extend into the upper case 22, and a rectangular hole corresponding to the display 23 is provided in the top cover 21.

Figure 8:
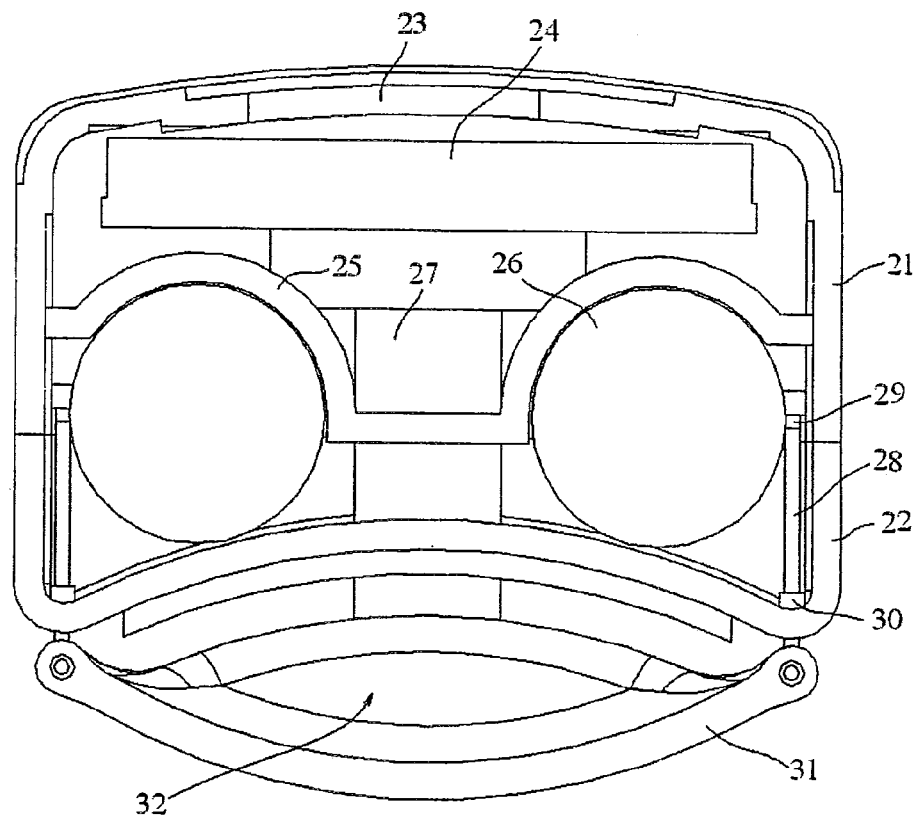
FIG. 8 is a transversal sectional view of the finger-clipped oximeter according to the second embodiment of the present invention.
Figure 10:
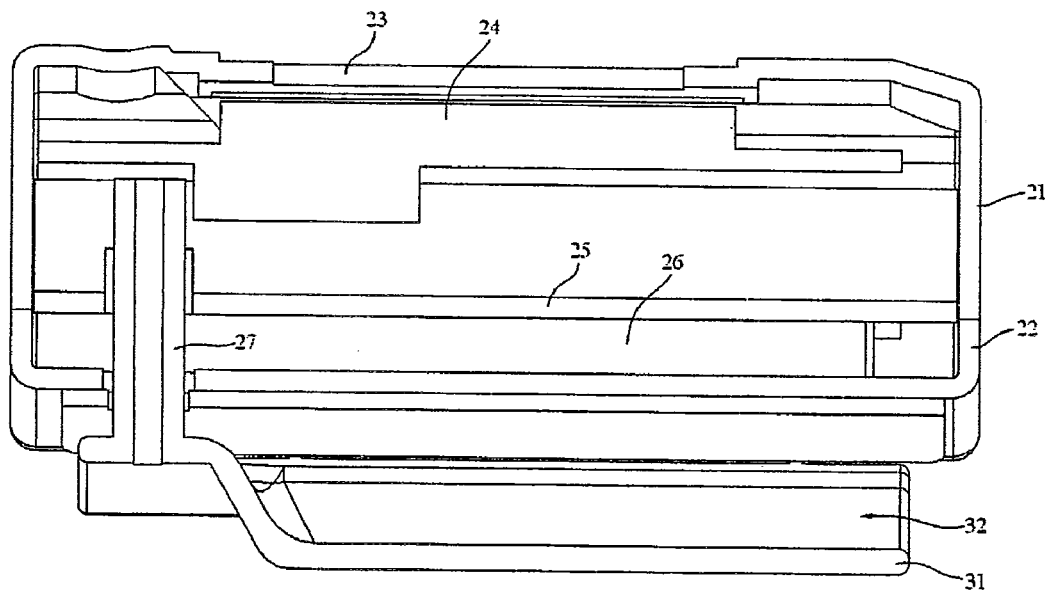
FIG. 10 is another longitudinal sectional view of the finger-clipped oximeter according to the second embodiment of the present invention.

In this embodiment, as shown in FIGS. 8 and 10, the finger pressed plate 31 can keep contact with a finger following the outline of the finger belly, and the upper case 22 provides a power supply and performs data processing and data display.

Figure 6:
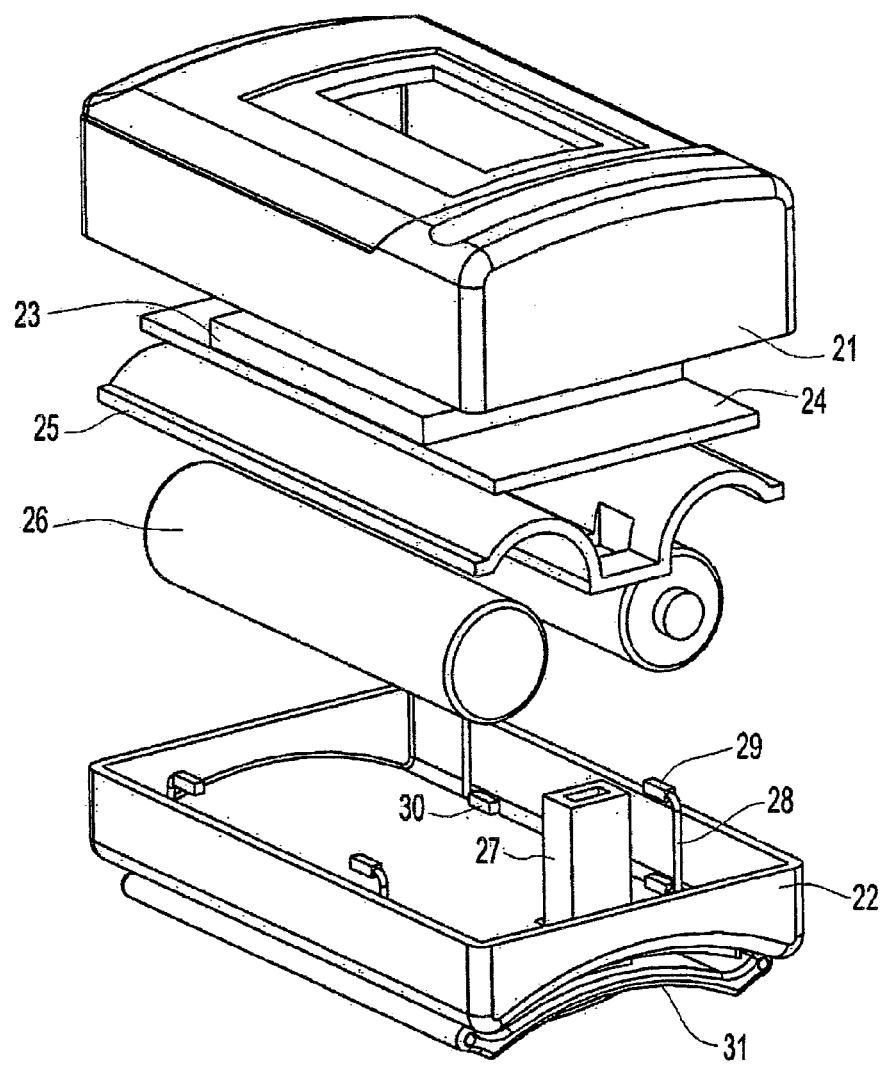
FIG. 6 is an exploded perspective view of a finger-clipped oximeter according to a second embodiment of the present invention.
Figure 7:
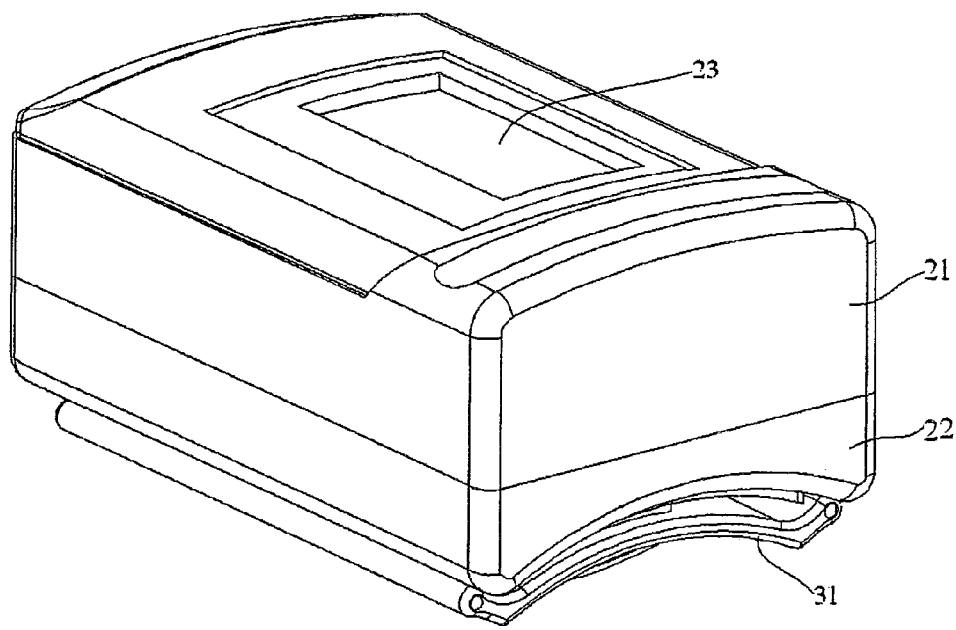
FIG. 7 is an overall perspective view of the finger-clipped oximeter according to the second embodiment of the present invention.

It can be seen most clearly from FIGS. 6 and 10 that the rectangular column 27 is provided on the finger pressed plate 31, the rectangular through hole corresponding to the rectangular column 27 is provided in the upper case 22, and the rectangular column 27 can pass through the rectangular through hole to extend into the upper case 22. The finger pressed plate 31 is directed by the rectangular through hole to ascend or descend, and the state in which the finger pressed plate 31 and the upper case 22 keep close contact with the finger imposes a restriction effect on an ascending or descending stroke of the rectangular column 27. In addition, the rectangular through hole can prevent the finger pressed plate 31 from being rotated excessively around the rectangular column 27; meanwhile, conducting wires of the power supply and signals can pass through the rectangular through hole to be connected to a measuring element (not shown) in the finger pressed plate 31.

Figure 9:
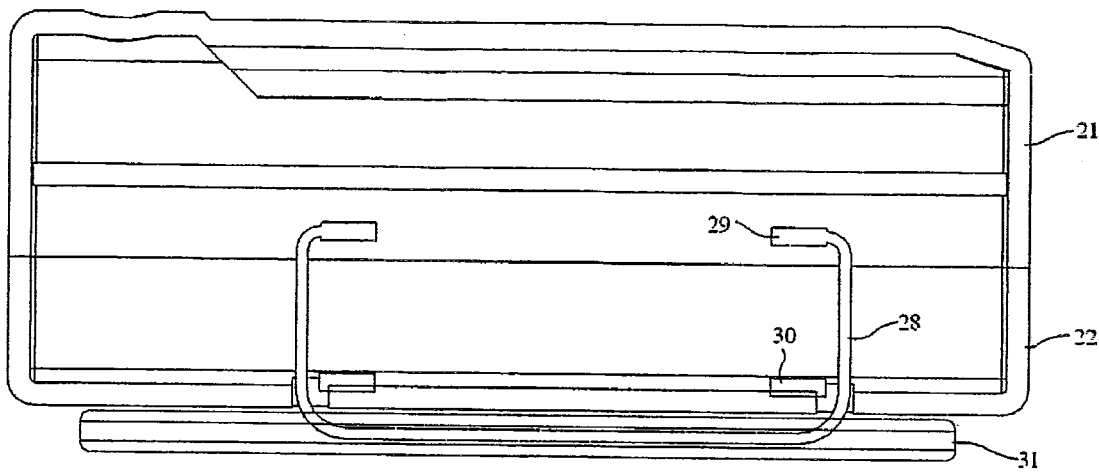
FIG. 9 is a longitudinal sectional view of the finger-clipped oximeter according to the second embodiment of the present invention.

In this embodiment, as shown in FIGS. 6, 8 and 9, one U-shaped connecting rod 28 is provided at each of two longitudinal edges of the oximeter having the finger pressed plate 31 respectively, and the middle portion of each U-shaped connecting rod 28 is a straight portion which extends through an edge portion on a side of the finger pressed plate 31 and is embedded in the finger pressed plate 31. Two arm portions of each U-shaped connecting rod 28 are inserted into the upper case 22 to serve as a connecting piece between the upper case 22 and the finger pressed plate 31. One movable magnet 29 is provided at each end of the two arm portions of each U-shaped connecting rod 28 respectively, therefore in this embodiment, the oximeter having the finger pressed plate 31 is provided with four movable magnets 29 totally; meanwhile, one stationary magnet 30 which is aligned with one of the movable magnets 29 in the vertical direction is provided at each of four corners of a bottom wall of the upper case 22 respectively. The movable magnets 29 may be ferrite magnets. The four pairs of magnets are arranged in such manner that the same magnetic poles in each pair are opposed to each other, that is, the N pole of one movable magnet is opposed to the N pole of one stationary magnet, or the S pole of one movable magnet is opposed to the S pole of one stationary magnet. Thus, each pair of one movable magnet and one stationary magnet act as a function of repelling mutually.

When the finger pressed plate 31 is pressed down by a finger, the distance between each pair of magnets 29 and 30 is reduced and the repelling force is increased so that the finger pressed plate 31 tends to keep contact with the finger. Since a force is applied in a non-mechanical manner in the second embodiment, no failure of mechanical movement occurs.

There is a large moving stroke between the magnets 29 and 30, as a result, both a user with thick fingers and a user with thin fingers can use the oximeter. Further, when the finger pressed plate 31 ascends or descends in a direction which is not parallel to that of the upper case 2 in order to accommodate to the change of thickness from the finger root to the finger tip, the finger pressed plate 31 can be rotated freely around the rectangular column 27 in both the vertical direction and the horizontal direction for a small angle so that the finger is very comfortable during the measurement.

Moreover, during this procedure, the magnets 29 and 30 are not influenced by the rotational force, and the two side arms of each of the U-shaped connecting pieces are expanded or contracted in the upper case 22 smoothly so that the finger pressed plate 31 can slide up and down with respect to the upper case 22 smoothly.

According to the second embodiment of the present invention, as shown in FIGS. 6 to 10, the main operation procedure of the finger-clipped oximeter is as follows. When a user inserts a finger into the finger inserting hole 32, the finger pressed plate 31 is pressed downward by the finger belly, and the rectangular column 27 fixed on the finger pressed plate 31 is directed by the rectangular through hole in the upper case 22 to move downward; meanwhile, the distance between each pair of magnets 29 and 30 is reduced so as to provide an enough stroke for the finger to be inserted into the finger inserting hole 32.

When the user pulls his finger out of the finger inserting hole 32, the finger pressed plate 31 is not pressed downward by the finger belly any more, and the rectangular column 27 fixed on the finger pressed plate 31 is directed by the rectangular through hole in the upper case 22 to move upward; meanwhile, the distance between each pair of magnets 29 and 30 are restored to the original distance, and the finger inserting hole 32 is closed.

In other embodiments, the middle portion of each U-shaped connecting rod can be pressure-cast to an edge portion on a side of the finger pressed plate to dispense with the rectangular columns 7 and 27 which are provided in the upper case for directing the two arm portions of each U-shaped connecting rod.

Particularly, at least a portion of the middle portion of each U-shaped connecting rod has a structure which can prevent the U-shaped connecting rods from being rotated with respect to the finger pressed plate. For example, at least a portion of the middle portion of each U-shaped connecting rod can be made into a pyramid shape or be provided with fins.

Particularly, a V-shaped portion which extends toward the middle portion of each U-shaped connecting rod is provided at each end of the two arm portions of each U-shaped connecting rod respectively. In the first embodiment, the V-shaped portion is opened toward two sides of each U-shaped connecting rod; in other embodiments, the V-shaped portion is opened toward each straight portion in the middle portion of each U-shaped connecting rod.

Although several embodiments of the present invention have been to described, it should be understood by those skilled in the art, various modifications, improvements and substitutions can be made to the present invention, all of which will fall within the scope of the invention defined by the appended claims.

What is claimed is:

1. A finger-clipped oximeter, wherein the finger-clipped oximeter comprises:
   an upper case in which batteries and a display are provided, a rectangular through hole being provided in the upper case;

a finger pressed plate, a finger inserting hole being formed between an upper surface of the finger pressed plate and a lower surface of the upper case, a rectangular column with a position corresponding to that of the rectangular through hole of the upper case being provided on the finger pressed plate; and a pair of connectors which are capable of ascending or descending, each of the connectors including one U-shaped connecting rod, a middle portion of the U-shaped connecting rod being a straight portion which extends through an edge portion on a side of the finger pressed plate, two arm portions of the U-shaped connecting rod being inserted into the upper case to serve as a connecting piece between the upper case and the finger pressed plate.

2. The finger-clipped oximeter according to claim 1, wherein the middle portion of the U-shaped connecting rod is pressure-cast to an edge portion on a side of the finger pressed plate.

3. The finger-clipped oximeter according to claim 2, wherein at least a portion of the middle portion of the U-shaped connecting rod has a structure which can prevent the U-shaped connecting rod from being rotated with respect to the finger pressed plate.

4. The finger-clipped oximeter according to claim 1, wherein at least one column like portion which extends straight up is provided at each of four corners of an upper surface of a bottom wall of the upper case, and positions of the two arm portions of the U-shaped connecting rod are limited by the at least one column like portion.

5. The finger-clipped oximeter according to claim 1, wherein the upper case has a top cover.

6. The finger-clipped oximeter according to claim 1, wherein the finger pressed plate is made of plastics or silica gel.

7. The finger-clipped oximeter according to claim 1, wherein a V-shaped portion which extends toward the middle portion of the U-shaped connecting rod is provided at each end of the two arm portions of the U-shaped connecting rod.

8. The finger-clipped oximeter according to claim 7, wherein the V-shaped portion is opened toward two sides of the U-shaped connecting rod, or is opened toward the straight portion in the middle portion of the U shaped connecting rod.

9. The finger-clipped oximeter according to claim 1, wherein one movable magnet is provided at each end of the two arm portions of the U-shaped connecting rod, while one stationary magnet is provided at each root of the two arm portions of the U-shaped connecting rod, and the movable magnet and the stationary magnet are provided so that magnetic poles with the same polarity are opposed to each other.

* * * * *